United States Patent
Wu

(10) Patent No.: US 9,504,561 B2
(45) Date of Patent: Nov. 29, 2016

(54) SYSTEMS AND PROCESSES FOR INSERTING AN INTRAOCULAR LENS

(71) Applicant: NOVARTIS AG, Basel (CH)

(72) Inventor: Yinghui Wu, Cedar Hill, TX (US)

(73) Assignee: Novartis AG, Basel (CH)

( * ) Notice: Subject to any disclaimer, the term of this patent is extended or adjusted under 35 U.S.C. 154(b) by 264 days.

(21) Appl. No.: 14/162,463

(22) Filed: Jan. 23, 2014

(65) Prior Publication Data

US 2014/0257315 A1 Sep. 11, 2014

Related U.S. Application Data

(60) Provisional application No. 61/774,379, filed on Mar. 7, 2013.

(51) Int. Cl.
*A61F 2/16* (2006.01)

(52) U.S. Cl.
CPC ..................................... *A61F 2/167* (2013.01)

(58) Field of Classification Search
CPC .... A61F 2/1662; A61F 2/167; A61F 2/1678; A61F 2/1691
See application file for complete search history.

(56) References Cited

U.S. PATENT DOCUMENTS

| | | | | |
|---|---|---|---|---|
| 5,494,484 A * | 2/1996 | Feingold | | A61F 2/1678 206/5.1 |
| 5,643,276 A * | 7/1997 | Zaleski | | A61F 2/1667 606/107 |
| 7,357,426 B2 * | 4/2008 | Bormioli | | F16L 37/62 137/614.05 |
| 2001/0007075 A1 | 7/2001 | Hjertman et al. | | |
| 2001/0044628 A1 * | 11/2001 | Portney | | A61F 2/1664 606/107 |
| 2008/0119865 A1 * | 5/2008 | Meunier | | A61F 2/1678 606/107 |
| 2009/0112223 A1 * | 4/2009 | Downer | | A61F 2/1667 606/107 |
| 2010/0121340 A1 * | 5/2010 | Downer | | A61F 2/167 606/107 |
| 2010/0125278 A1 * | 5/2010 | Wagner | | A61F 2/167 606/107 |
| 2010/0204704 A1 | 8/2010 | Davies et al. | | |

(Continued)

FOREIGN PATENT DOCUMENTS

| | | |
|---|---|---|
| CN | 1177919 A | 4/1998 |
| CN | 1185100 A | 6/1998 |

(Continued)

OTHER PUBLICATIONS

International Search Report and Written Opinion of the International Searching Authority, International Application No. PCT/US14/15204, dated Apr. 29, 2014, 6 pages.

(Continued)

*Primary Examiner* — Julie A Szpira
(74) *Attorney, Agent, or Firm* — Darien Reddick

(57) ABSTRACT

Various systems and techniques for inserting an intraocular lens are disclosed. In particular implementations, a system and a technique for inserting an intraocular lens may include the ability to move, in response to a force being applied in a first direction along a longitudinal axis, a first plunger tip along the longitudinal axis and into a delivery cartridge to fold an intraocular lens and move in a second direction along the longitudinal axis in response to the applied force being reduced. The system and the technique may also include the ability to engage a second plunger tip and move, in response to a force being applied in the first direction along the longitudinal axis, the second plunger tip along the longitudinal axis and into the delivery cartridge to insert the intraocular lens.

23 Claims, 7 Drawing Sheets

(56) References Cited

U.S. PATENT DOCUMENTS

2011/0172676 A1 7/2011 Chen
2011/0264101 A1* 10/2011 Inoue .................... A61F 2/1678
606/107

FOREIGN PATENT DOCUMENTS

CN 101467925 A 7/2009
WO 2007098622 9/2007

OTHER PUBLICATIONS

International Preliminary Report on Patentability and Written Opinion of the International Searching Authority, International Application No. PCT/US2014/015204, dated Sep. 8, 2015, 5 pages.
Supplemental European Search Report for Application No. 14761046.3, Publication No. EP2925260, Published Oct. 7, 2015, dated Nov. 6, 2015, 2 pages.

* cited by examiner

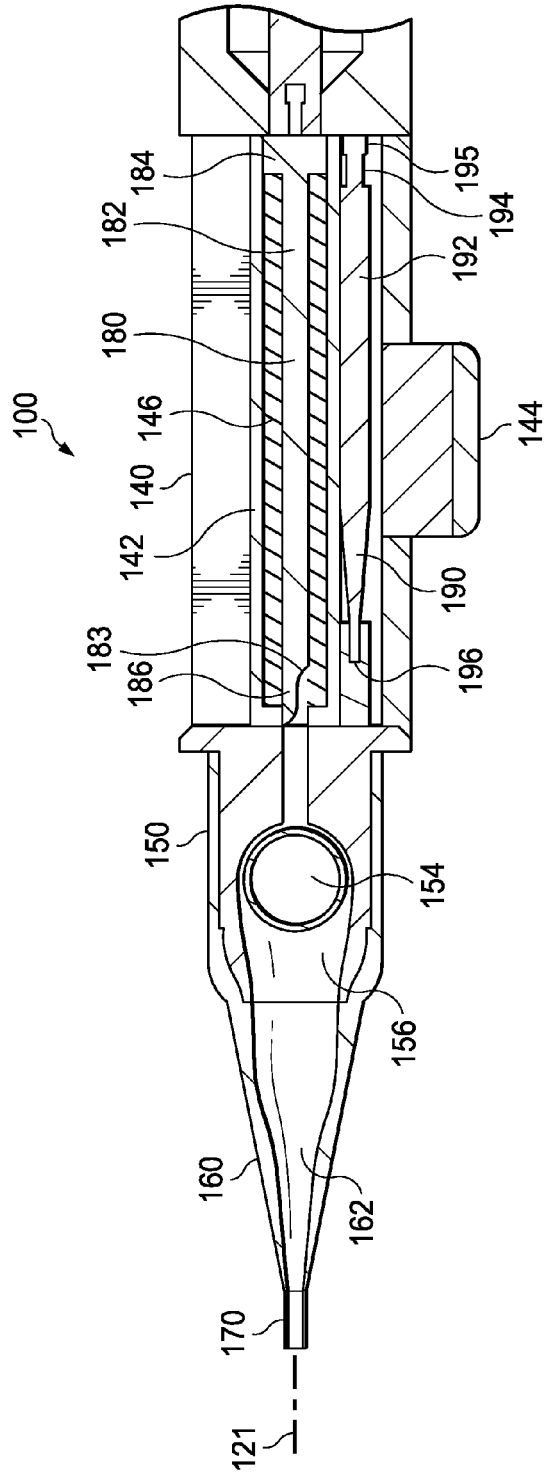
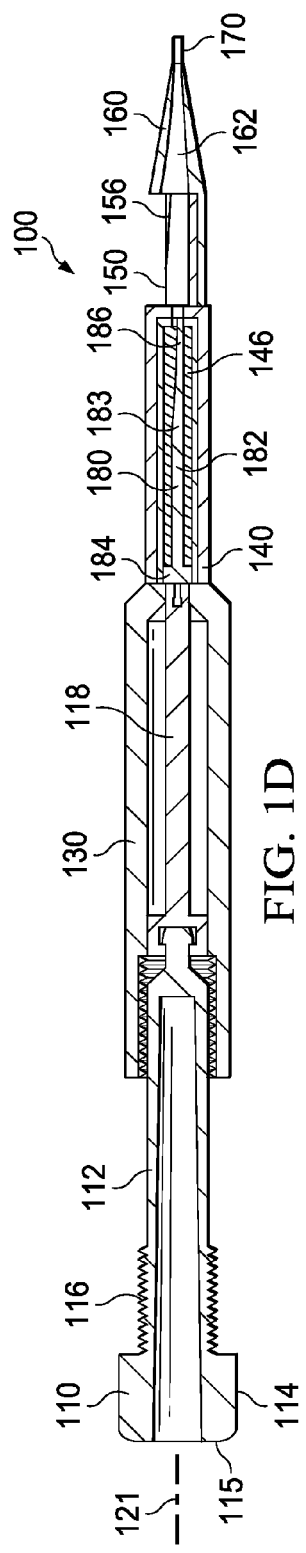
FIG. 1C
FIG. 1D

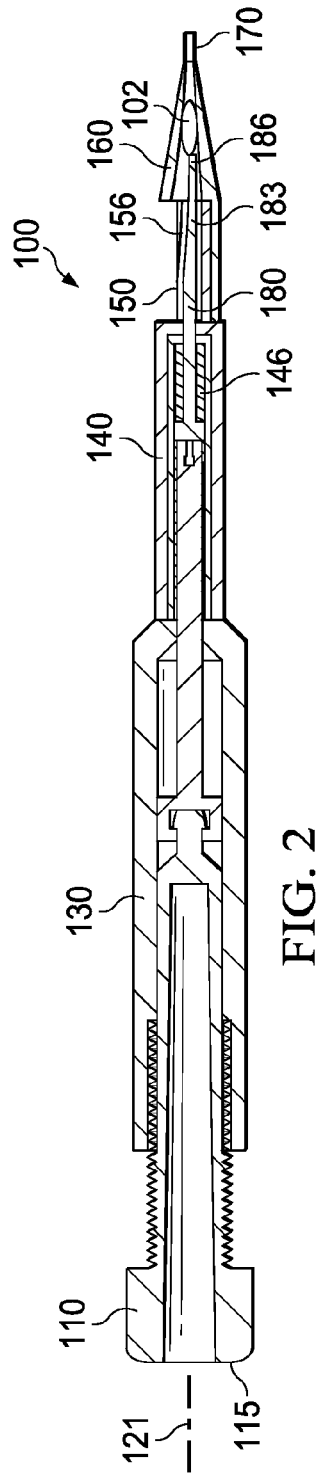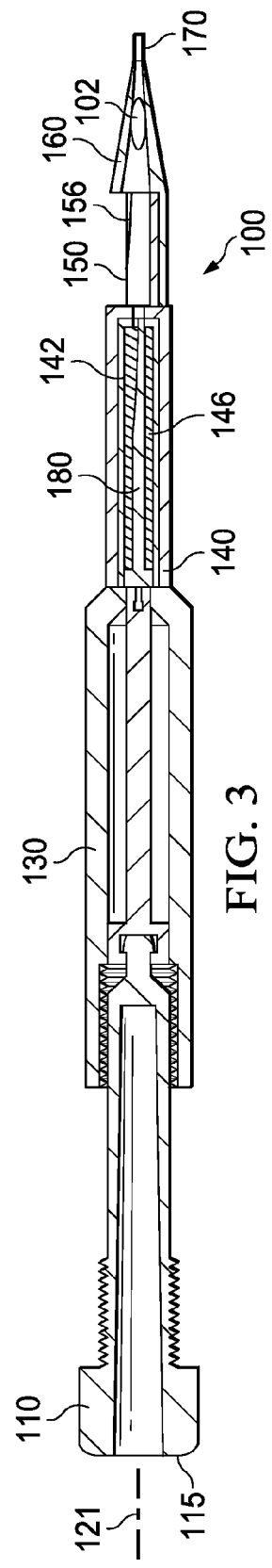

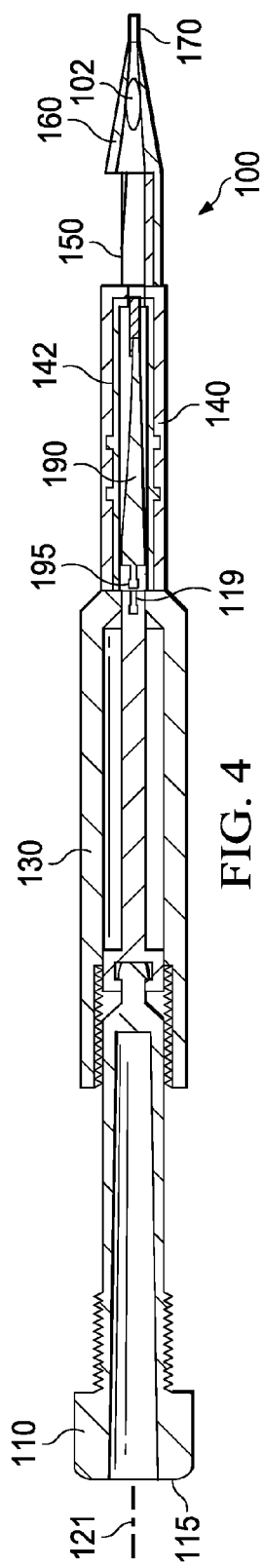
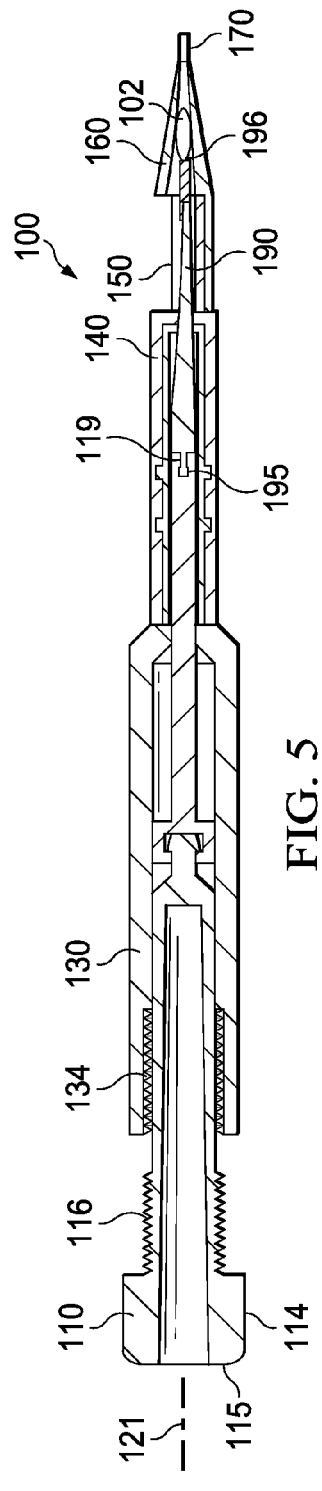
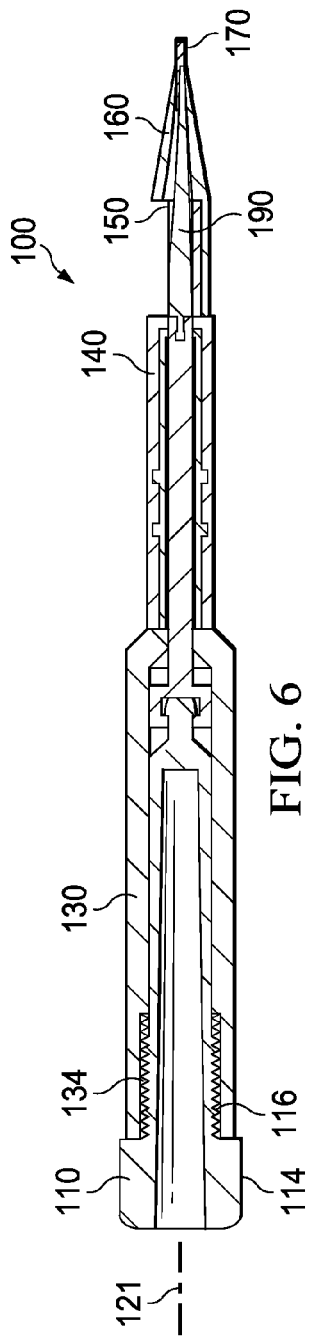
FIG. 4
FIG. 5
FIG. 6

SYSTEMS AND PROCESSES FOR INSERTING AN INTRAOCULAR LENS

CROSS REFERENCE TO RELATED APPLICATIONS

This application claims the benefit of U.S. Provisional Application No. 61/774,379 filed Mar. 7, 2013, the entire contents being incorporated herein by reference.

BACKGROUND

The present disclosure relates to optical surgery, and more specifically to surgery for replacement of a patient's lens.

The human eye, in simple terms, functions to provide vision by transmitting and refracting light through a clear outer portion called the cornea and focusing the image by way of the lens onto the retina at the back of the eye. The quality of the focused image depends on many factors including the size, shape, and length of the eye, and the shape and transparency of the cornea and lens.

When trauma, age, or disease causes the lens to become less transparent, vision deteriorates because of a reduction in light transmitted to the retina. This deficiency in the eye's lens is medically known as a cataract. The treatment for this condition is often surgical removal of the lens and implantation of an artificial lens, often termed an intraocular lens (interchangeable referred to as "IOL").

An IOL is often foldable and inserted into the eye through a relatively small incision by being advanced through an insertion cartridge, which causes the IOL to fold. The IOL is typically advanced through the insertion cartridge by a plunger-like device.

SUMMARY

Various preload IOL delivery systems and techniques for inserting an intraocular lens are disclosed. In one general implementation, a system for inserting an intraocular lens may include a plunger, a plunger chamber, a plunger tip chamber, a lens chamber, and a delivery cartridge. The lens chamber may be adapted to receive an intraocular lens, and the delivery cartridge may be coupled to the lens chamber and adapted to fold and compress an intraocular lens as it is moved therethrough. The plunger tip chamber may be adapted to house a first plunger tip and a second plunger tip and to switch between the plunger tips that may engage the plunger and an intraocular lens. In certain implementations, the first plunger tip has a first hardness and the second plunger tip has a second hardness, and the hardness of the first plunger tip is substantially greater than the hardness of the second plunger tip. The plunger may be adapted to be manipulated by a user, and the plunger chamber may be adapted to allow the plunger to be moved therein along a longitudinal axis and move a plunger tip along the longitudinal axis.

In certain implementations, the plunger tip chamber may be adapted to alternatingly switch between alignment of the first plunger tip with the plunger and alignment of the second plunger tip with the plunger. The plunger tip chamber may, for example, alter which plunger tip is aligned with the plunger by being laterally moveable so as to alternatingly align the first plunger tip with the plunger and the second plunger tip with the plunger. The plunger tip chamber may, for instance, include a cassette adapted to hold the first plunger tip and the second plunger tip and to move laterally within the plunger tip chamber to align alternatingly the first plunger tip and the second plunger tip with the plunger. In particular implementations, the cassette may be adapted to lock into a first position in which the first plunger tip is aligned with the plunger and to lock into a second position in which the second plunger tip is aligned with the plunger.

The plunger tip chamber may also include a spring adapted to compress when the first plunger tip advances. The spring may be adapted to retract the first plunger tip and the plunger when the first plunger tip is released.

In some implementations, the plunger is adapted to engage the first plunger tip via abutting contact. In some implementations, the plunger is adapted to engage the second plunger tip via an interlocking relationship. In particular implementations, the lens chamber may be adapted to prevent advancement of the first plunger tip beyond a predetermined distance. The predetermined distance may correspond to a distance associated with substantially folding an intraocular lens.

The system may also include an insertion tip coupled to the delivery cartridge. The insertion tip may be adapted to be inserted in an eye for injection of a folded, compressed intraocular lens. The insertion tip may be made from a different material and coupled or overmolded to the delivery cartridge.

In one general implementation, a process for inserting an intraocular lens may include moving, in response to a force being applied in a first direction along a longitudinal axis, a first plunger tip along the longitudinal axis and into a delivery cartridge to fold an intraocular lens and moving in a second direction along the longitudinal axis in response to the applied force being released. The apparatus performing the moving function may, for example, be a plunger. The process may also include engaging a second plunger tip and moving, in response to a force being applied in the first direction along the longitudinal axis, the second plunger tip along the longitudinal axis and into the delivery cartridge to compress the intraocular lens.

In some implementations, moving in a second direction along the longitudinal axis in response to the applied force being released may include returning the first plunger tip to a plunger tip chamber. In certain implementations, engaging a second plunger tip may include altering which plunger tip is aligned with the longitudinal axis.

In particular implementations, altering which plunger tip is aligned with the longitudinal axis may include laterally moving the first plunger tip from being aligned with the longitudinal axis and aligning the second plunger tip with the longitudinal axis. Laterally moving the first plunger tip from being aligned with the longitudinal axis and aligning the second plunger tip with the longitudinal axis may, for example, include laterally moving a cassette adapted to hold the plunger tips. The process may also include locking the cassette in a position in which the second plunger tip is aligned with the longitudinal axis.

In certain implementations, moving in a second direction along the longitudinal axis in response to the applied force being reduced may include decompressing a spring.

The process may also include stopping movement of the first plunger tip in the first direction after the first plunger tip has traveled a predetermined distance.

Various implementations may have one or more features. For example, by being able to use plungers in sequence, a relatively hard tip plunger and a relatively soft plunger tip may be used to first appropriately fold an intraocular lens and still compress it sufficiently to fit through a small tip with little to no damage. Thus, the benefits of both a hard-tip plunger and a soft-tip plunger may be realized at the same time to reduce tip size and meet the demanding performance requirements of micro-incision cataract surgery.

Various other features will be apparent to those skilled in the art from the following description and the accompanying figures.

BRIEF DESCRIPTION OF THE DRAWINGS

FIG. 1C is a cross-sectional view of a distal end of an example system for compacting an intraocular lens.

FIG. 1D is a cross-sectioned side view of a portion of an example system for compacting an intraocular lens.

FIG. 2 is a cross-sectional side view of an example system for compacting an intraocular lens in which a first plunger tip is extended by a plunger.

FIG. 3 is a cross-sectional side view of an example system for compacting an intraocular lens in which the first plunger tip is retracted.

FIG. 4 is a cross-sectional side view of an example system for compacting an intraocular lens in which a second plunger tip is aligned with a plunger.

FIG. 5 is a cross-sectional side view of an example system for compacting an intraocular lens in which the second plunger tip is partially extended.

FIG. 6 is a cross-sectional side view of an example system for compacting an intraocular lens in which the second plunger tip is substantially fully extended.

DETAILED DESCRIPTION

Figure 1A:
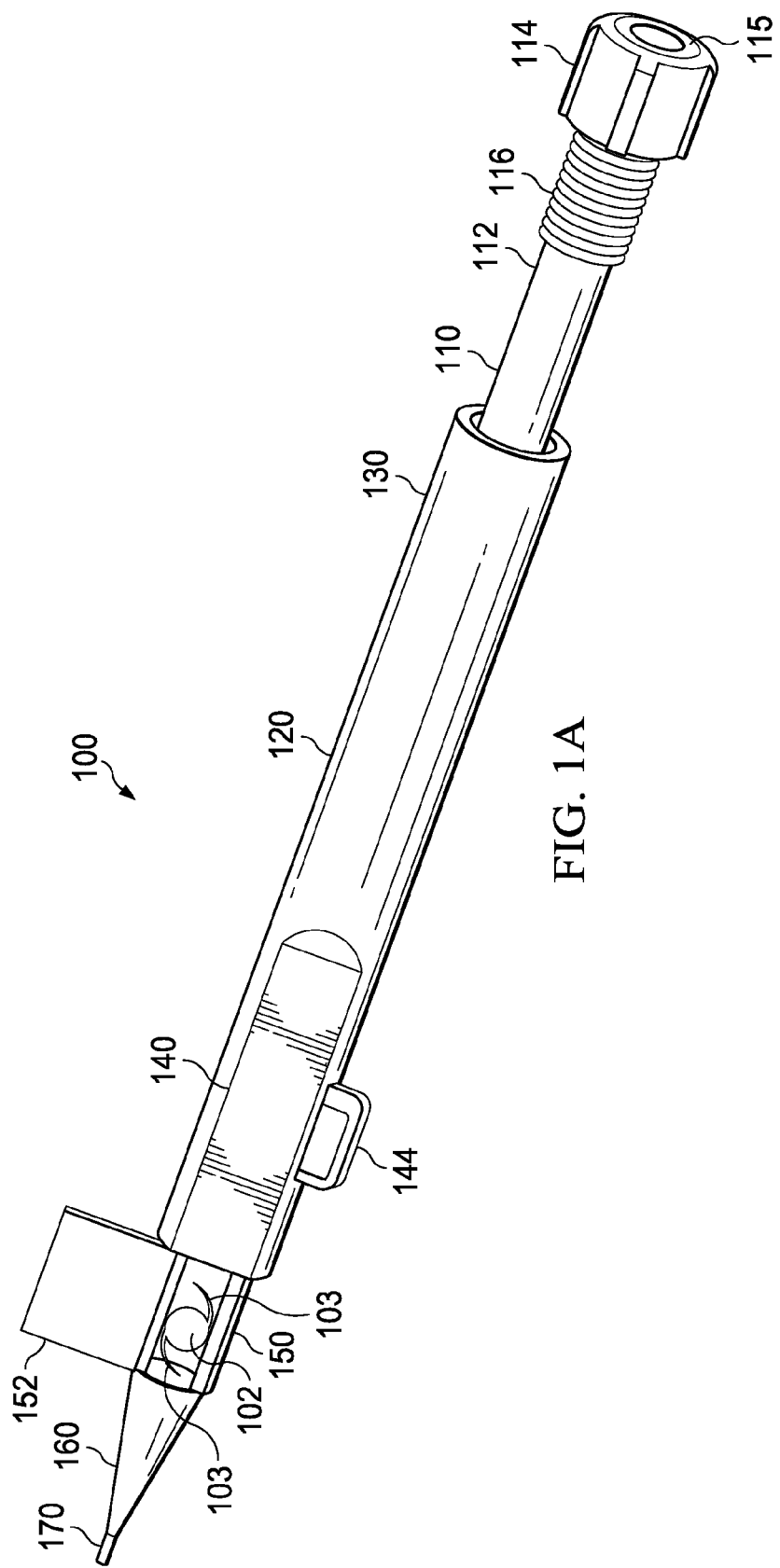
FIG. 1A is a perspective view of an example system for compacting an intraocular lens.
Figure 1B:
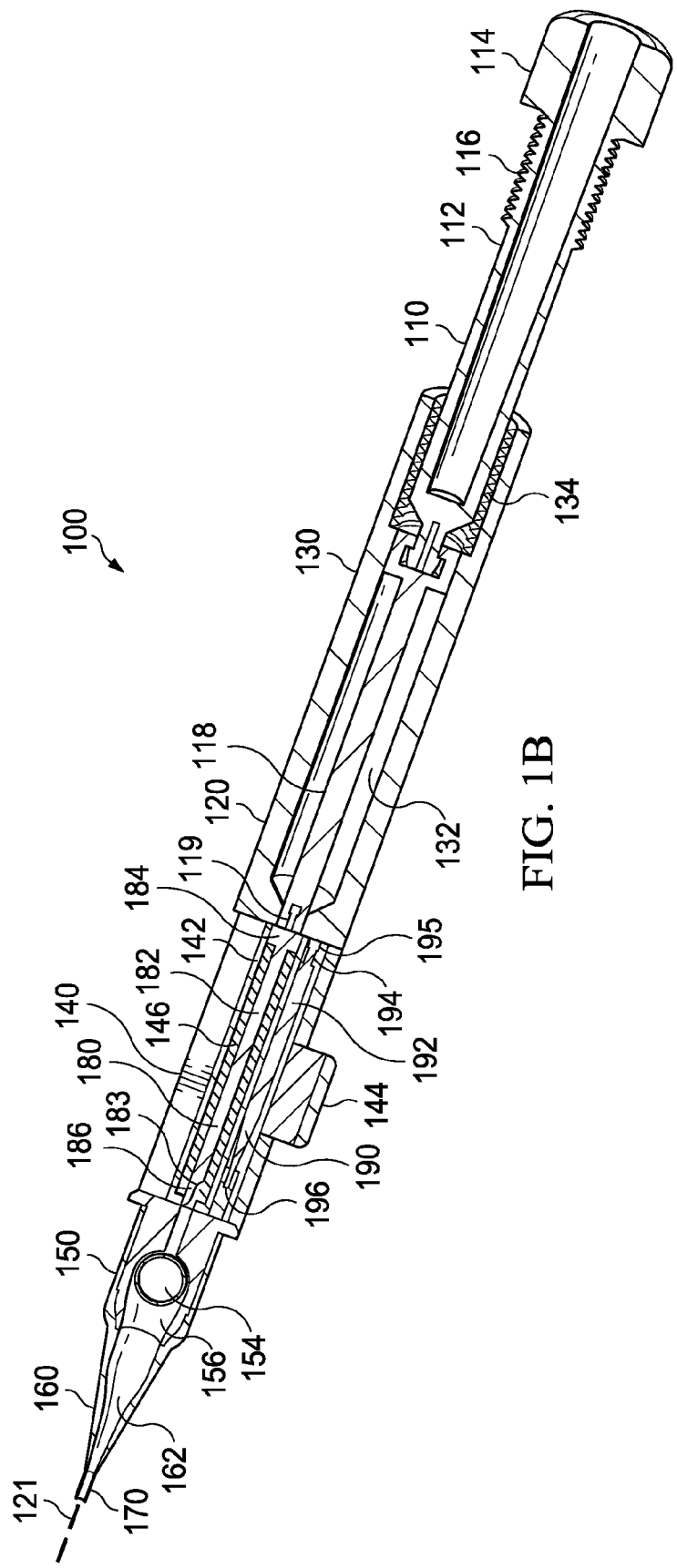
FIG. 1B is a cross-sectional side view of an example system for compacting an intraocular lens.

FIGS. 1A-1D illustrate an example system 100 for compacting an IOL 102. IOL 102, which is typically composed of silicone, soft acrylics, hydrogels, or other appropriate materials, is advanced through system 100 in preparation for insertion into the eye. In some instances, an IOL 102 may, for example, be approximately 13 mm in diameter and may include haptics 103. Surgical incisions may be much smaller (e.g., 0.5-3 mm in width). The IOL is therefore typically compacted (e.g., folded and compressed) before insertion through the incision.

In general, system 100 includes a plunger 110 and a housing 120. Plunger 110 is manipulable by a user to advance IOL 102 through housing 120. During this advancement, IOL 102 is folded and compressed for injection into an eye. Plunger 110 and housing 120 may generally be made of hard plastic or any other appropriate material.

In more detail, plunger 110 includes a body 112 and a user interface 114. Housing 120 includes a plunger chamber 130, a plunger tip chamber 140, a lens chamber 150, a delivery cartridge 160, and an insertion tip 170, which may be integrally formed with each other. Housing 120 has a longitudinal axis 121 along which plunger 110 and various components of housing 120 move.

In the illustrated implementation, body 112 of plunger 110 is generally elongated and is cylindrical in the illustrated implementation. In other implementations, body 112 may have other sizes and configurations that allow it to move within a housing. User interface 114 is sized and shaped to allow a user to grasp it and to press on one of its ends 115 to advance plunger 110 through housing 120. Plunger 110 also includes threads 116, whose operation will be discussed in more detail below. Plunger 112 further includes a plunger adapter 118. Plunger adapter 118 allows plunger 110 to interface with a number of plunger tips, which will be discussed below. The end of plunger adapter 118 distal from end 115 includes a notch 119 for engaging (e.g., mating with) one or more plunger tips.

Plunger chamber 130 is generally elongated and is cylindrical in the illustrated implementation. Plunger chamber 130 has a passage 132 sized to allow body 112 of plunger 112 to pass therethrough. Plunger chamber 130 also includes threads 134. Threads 134 are sized to mate with threads 116 of plunger 110.

Plunger tip chamber 140 includes a cassette 142 that holds a first plunger tip 180 and a second plunger tip 190. Cassette 142 is moveable laterally relative to longitudinal axis 121. To move cassette 142, cassette 142 includes a tab 144 that extends outside of housing 120. By pressing on tab 144, cassette 142 may be moved laterally (e.g., by sliding). Cassette 142 also includes a spring 146 that is compressed as first plunger tip 180 is moved towards lens chamber 150.

Lens chamber 150 is adapted to receive IOL 102 before a surgical procedure begins. Lens chamber 150 includes a cover 152 that may be opened to allow insertion of IOL 102. In particular implementations, cover 152 may allow IOL 102 to be inserted into lens chamber 150 before shipment. System 100 may then be cleaned, sterilized, and packaged for shipment. System 100 may therefore be a single-use (e.g., disposable) device. In other implementations, IOL 102 may be inserted in system 100 shortly before use. Lens chamber 150 also includes a lens well 154 and a tapered wall portion 156. Lens well 154 is adapted to receive IOL 102 and hold it statically. Portions of the IOL 102 (e.g., haptics) may be folded upon insertion in lens well 154. Tapered wall portion 156 tapers toward insertion tip 170.

Delivery cartridge 160 is adapted to fold and compress IOL 102. In the illustrated implementation, delivery cartridge 160 has a circular cross-section and tapers towards insertion tip 170, although it could have other shapes (e.g., elliptical cross-section) in other implementations. Delivery cartridge 160 includes a chamber 162. Chamber 162 has a lumen that connects lens chamber 150 to insertion tip 170 and generally tapers from lens chamber 150 to insertion tip 170. The lumen of chamber 162 may facilitate the folding and compression of IOL 102.

Insertion tip 170 is generally cylindrical in shape and is sized to fit through a surgical incision in an eye and allow IOL 102 to pass therethrough. In particular implementations, insertion tip 170 may fit through an incision of less than 2 mm.

First plunger tip 180 includes a body 182, a head 184, and a lens engagement tip 186. Body 182 is elongated and may be cylindrical in particular implementations. Body 182 includes a portion 183 that tapers towards insertion tip 170. Tapered portion 183 is generally sized and shaped to match tapered wall portion 156 of delivery cartridge 150. Head 184 is wider than body 182 and may also be cylindrical in particular implementations. Head 184 is generally sized to reliably engage plunger 110. Lens engagement tip 186 includes a generally sloping surface, which assists in engaging and folding IOL 102. First plunger tip 180 may be made of hard plastic, stainless steel, titanium, or any other appropriate material.

Second plunger tip 190 also includes a body 192, a head 194, and a lens engagement tip 196. Body 192 is elongated and may be cylindrical in particular implementations. In the illustrated implementation, head 194 is narrower than body 192 and is cylindrical. However, in other implementations, the head 194 and/or the body 192 may have other cross-sectional shapes, e.g., elliptical. Head 194 includes a hub 195, which is sized to be received in notch 119 of plunger 110. Lens engagement tip 196 may be formed from a relatively compliant material. Body 192 and head 194 of second plunger tip 190 may be formed from a more rigid material. For example, the body 192 and the head 194 may be formed from a hard plastic, or other appropriate material. On the other hand, the lens engagement tip 196 may be formed from a relatively soft material (e.g., silicone rubber). The lens engagement tip 196 may be assembled on or overmolded onto body 192.

FIGS. 2-6 illustrate the operation of system 100. In certain modes of operation, system 100 arrives with IOL 102 already inserted in lens chamber 150. Then, when a user (e.g., physician or other medical profession) is ready to use system 100 (e.g., after sedating the patient, prepping the eye, and forming an incision in the cornea), the user may apply a longitudinal force to end 115 of plunger 110. Plunger 110 moves in response to the applied force along longitudinal axis 121 towards insertion tip 170. Due this motion, plunger 110 moves first plunger tip 180 along the longitudinal axis. Plunger 110 may or may not have been previously engaged with first plunger tip 180. If not previously engaged, the motion of plunger 110 may cause the two components to come into engagement.

As plunger 110 advances first plunger tip 180, lens engagement tip 186 of first plunger tip 180 engages IOL 102 in lens chamber 150. First plunger tip 180 then advances IOL 102 into delivery cartridge 160 to fold the IOL 120. The advancement of first plunger tip 180 is stopped after it has traveled a predetermined distance. In some instances, the advancement may be stopped when tapered portion 183 of first plunger tip 180 engages tapered wall portion 156 of lens chamber 150, as best shown in FIG. 2. The stoppage may, for example, occur when IOL 102 has been substantially folded. In the illustrated implementation, IOL 102 has adopted the lumen shape of the cartridge (e.g., the haptics and the optic body are folded in a stable and desired orientation), but compression has not yet begun.

The user may then reduce the force being applied to end 115 of plunger 110. Reducing the force sufficiently allows spring 146 to retract first plunger tip 180 in a second direction along longitudinal axis 121, while leaving IOL 102 folded in delivery cartridge 160. Spring 146 may, for example, cause first plunger tip 180 to substantially return to its original position in cassette 142, as shown in FIG. 3. In some implementations, plunger chamber 130 may include a detent (e.g., a small tab or ledge) to stop plunger 110 during the retraction.

The user may then engage tab 144 and move cassette 142 laterally relative to longitudinal axis 121. This movement disengages first plunger tip 180 from plunger 110. Thus, the first plunger tip is no longer aligned with longitudinal axis 121. The movement also aligns second plunger tip 190 with longitudinal axis 121, as best seen in FIG. 4. In some implementations, stops and/or locks may be used to control the movement of cassette 142 within the plunger tip chamber 140. For example, cassette 142 may engage (e.g., abut) portions of plunger chamber 140 to stop its motion. As another example, cassette 142 may include spring-like members (e.g., arms and/or detents) that engage one or more apertures recessed on the wall of plunger tip chamber 140.

The user may then apply a longitudinal force to end 115 of plunger 110. Plunger 110 again advances in response to the applied force along longitudinal axis 121 towards insertion tip 170. Due to this movement, notch 119 of plunger 110 mates with hub 195 of second plunger tip 190, as best shown in FIG. 5. Also due to this movement, lens engagement tip 196 engages with IOL 102. IOL 102 may have been resting in a folded state in delivery cartridge 160. Plunger 110 may then move the IOL 102 further into delivery cartridge 160, which further compacts (e.g., compresses) the IOL 102.

After sufficient movement, threads 116 of plunger 110 will engage (e.g., contact and/or mesh with) threads 134 of plunger chamber 130, as best seen in FIG. 5. IOL 102 may still be located in delivery cartridge 160 at this point. The user may then rotate user interface 114, which, after threads 116 and threads 134 mesh, will advance plunger 110 and, hence, second plunger tip 190 further towards the end of insertion tip 170, and result in final compaction of IOL 102, as best seen in FIG. 6. After further movement of plunger 110 due to the rotation, IOL 102 will reach the end of insertion tip 170 and be injected into an eye.

System 100 has a variety of features. For example, by being able to use a relatively hard plunger tip and a relatively soft plunger tip in sequence, IOL 102 may be folded appropriately and still compressed sufficiently to fit through a small (e.g., less than 2.2 mm) tip. This eliminates or substantially reduces the risk of damage that may occur to the IOL 102. Currently available soft-tipped plungers have the disadvantage of not being able to providing a secure and controlled IOL folding during early delivery stage, where a manual assistant IOL loading or folding is often needed for this kind of injector system. System 100, with two plungers concealed separately in the same device, incorporates the benefits of both a rigid-tip and soft-tip plunger at the same time to reduce tip size and meet the demanding performance requirements of micro-incision cataract surgery.

A variety of additions, deletions, substitutions, and modifications may be made to system 100 and still achieve compaction of an intraocular lens. For example, plunger 110 may not include threads 116. For instance, the intraocular lens may be inserted by just applying longitudinal forces to end 115, which may allow easier one-hand operation. As another example, first plunger tip 180 may include a hub to engage notch 119 of plunger 110. As a further example, second plunger tip 190 may not include a hub to engage notch 119. For instance, plunger 110 may just engage head 194 by contacting the head 194. As an additional example, plunger 110 may not include plunger adapter 118. As another example, plunger tip chamber 150 may include a lock to keep cassette 142 in place during transit and movement of first plunger tip 180.

Figure 7A:
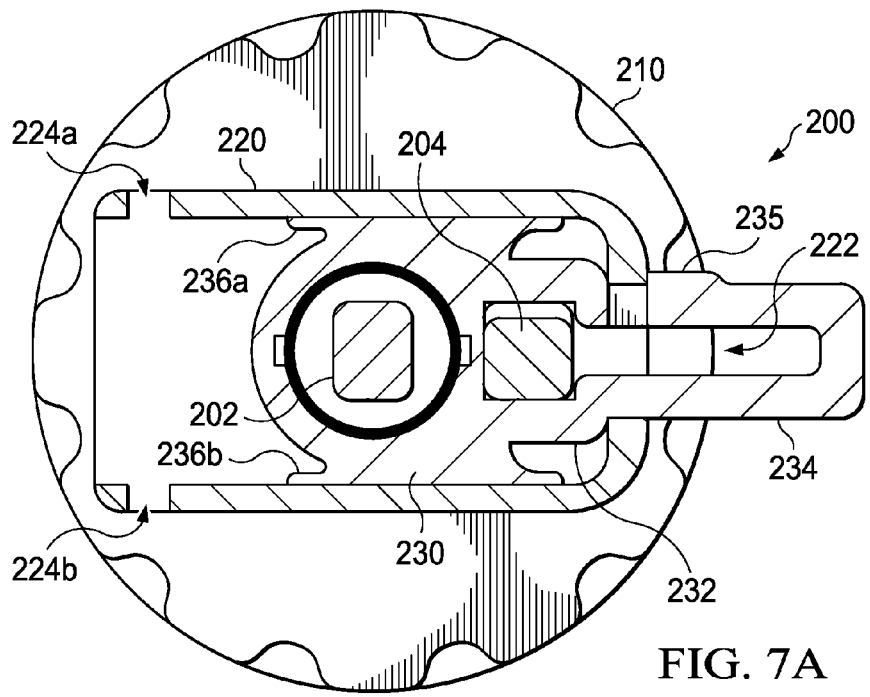
FIGS. 7A-7B are transverse cross-sectional views of a plunger chamber of an example system for compacting an intraocular lens.
Figure 7B:
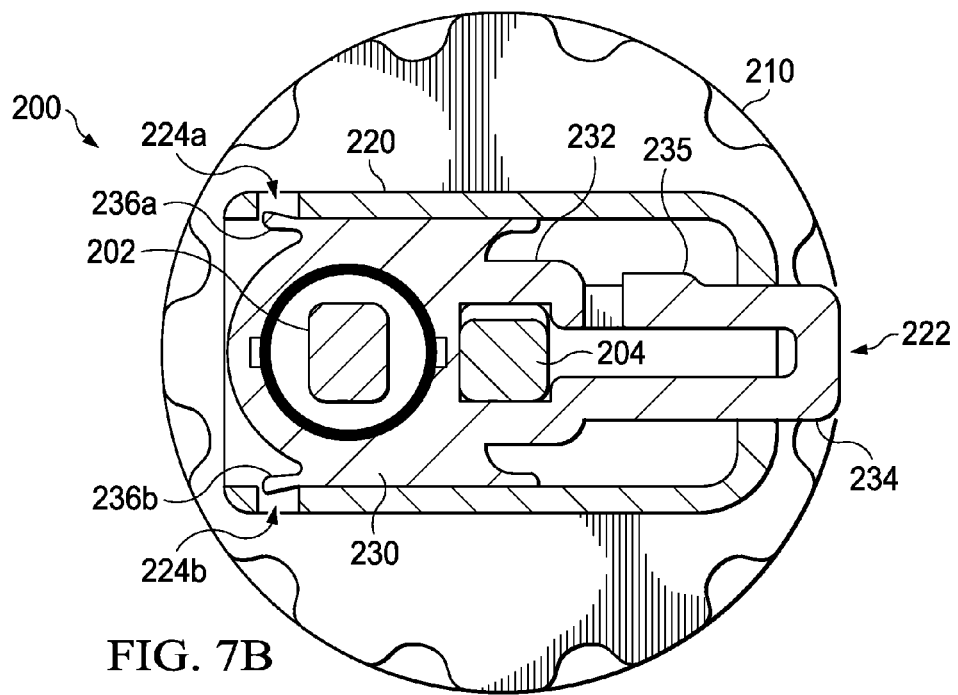

FIGS. 7A-7B illustrate a transverse cross-section of an example system 200 for compacting an intraocular lens. Elements of system 200 may be usable with system 100.

System 200 includes a plunger chamber 210 and a plunger tip chamber 220. In general, plunger chamber 210 is adapted to allow a plunger (not viewable) to move therein to advance a first plunger tip 202 and a second plunger tip 204 to engage and IOL. Plunger tip chamber 210 houses a cassette 230 that includes first plunger tip 202 and second plunger tip 204.

Cassette 230 includes a body 232 that holds first plunger tip 202 and second plunger tip 204. Cassette 230 also includes a tab 234 that extends from body 232 and arms 236*a*, 236*b* that extend from body 232. Tab 234 is adapted to be manipulated by a user and includes a detent 235, as shown in FIG. 7A. Detent 235 is used to secure cassette 230 in a first position in plunger tip chamber 220. Arms 236a, 236b are used to secure cassette 230 in a second position, as shown in FIG. 7B.

Plunger tip chamber 220 includes a first aperture 222 and second apertures 224a, 224b. First aperture 222 is sized to allow tab 234 to extend therethrough. Second apertures 224a, 224b are sized to allow arms 236a, 236b to extend thereinto.

In operation, cassette 230 is placed in the position shown in FIG. 7A before a surgical procedure (e.g., before shipping). In this position, first plunger tip 202, which may, for example, have a relatively hard tip, is aligned with the longitudinal axis of plunger chamber 210. Cassette 230 is held in this position by body 232 butting up against the inside of plunger tip chamber 220 and detent 235 engaging the outside of the plunger tip chamber 210. This arrangement holds first plunger tip 202 in place so that a plunger may engage the first plunger tip 202 appropriately.

When it is time to use second plunger tip 204, a user may engage tab 234 and move it inwards into plunger tip chamber 220. Detent 235 may be overcome by applied physical force and/or by being manipulated around the outside of plunger tip chamber 220 (e.g., by squeezing). As the user continues to move tab 234, body 232 moves so that arms 236a, 236b engage apertures 224a, 224b, as best seen in FIG. 7B. Arms 236a, 236b may, for example, engage apertures 224a, 224b by springing into them. When arms 236a, 236b engage apertures 224a. 224b, second plunger tip 204 is aligned with the longitudinal axis of plunger chamber 210. Thus, the plunger may now engage the second plunger tip 204.

Although FIG. 7 illustrates a system for compacting an intraocular lens, other systems for compacting an intraocular lens may include fewer, additional, and/or a different arrangement of components. For example, a system may include a lens chamber, a delivery cartridge, and/or an insertion tip. As another example, a system may not include one or more locking mechanisms, e.g., detent 235 and/or arms 236a, 236b and corresponding apertures 224a, 224b.

Figure 8:
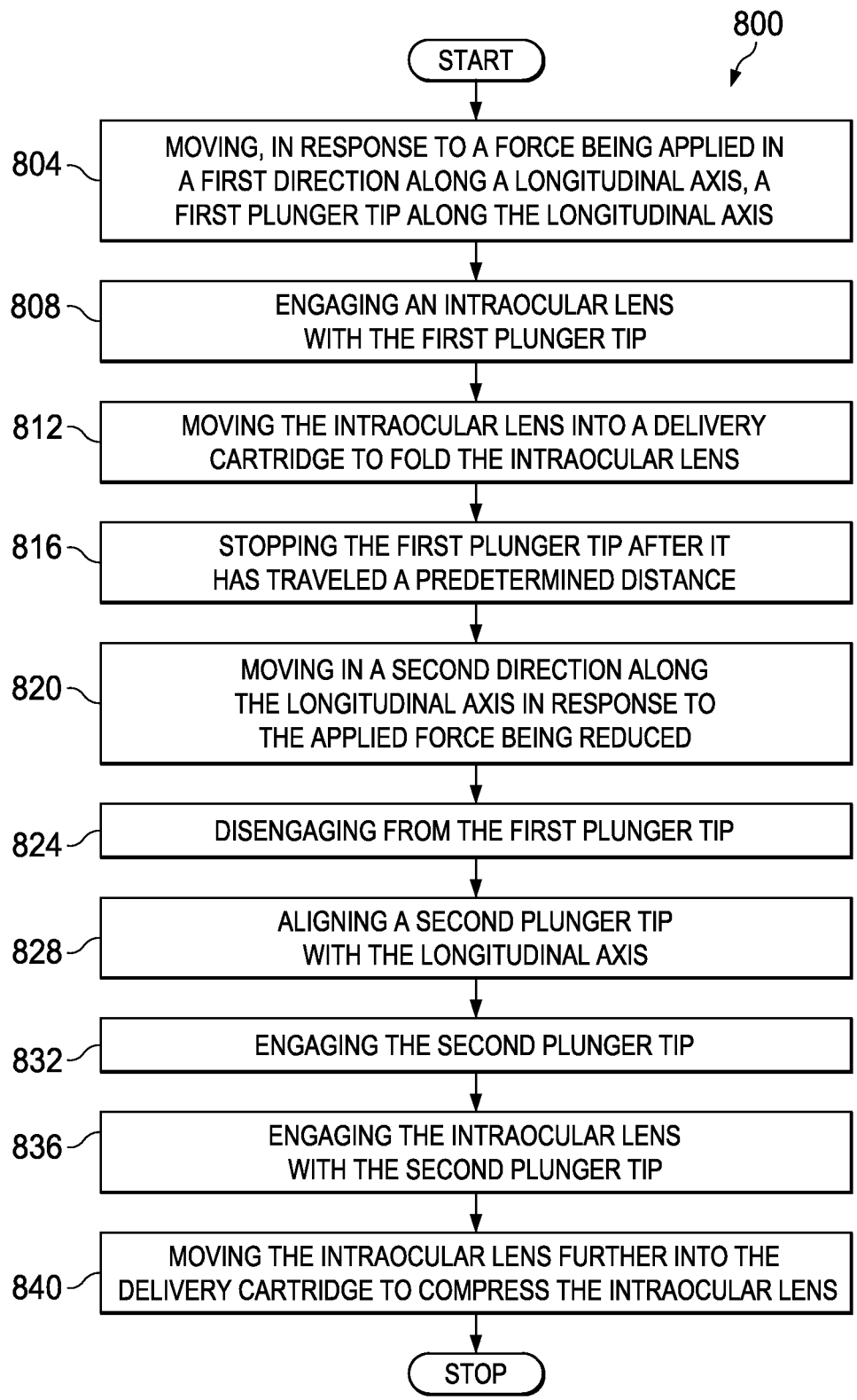
FIG. 8 is a flowchart illustrating an example process for compacting an intraocular lens.

FIG. 8 illustrates an example process 800 for compacting an intraocular lens. Process 800 may, for example, be implemented by a system similar to system 100. Other lens compaction systems may also implement the process.

Process 800 calls for moving, in response to a force being applied in a first direction along a longitudinal axis, a first plunger tip along the longitudinal axis (operation 804). The movement may, for example, be accomplished by a plunger that is moved in response to the applied force. The plunger may have been previously engaged with the first plunger tip or may become engaged with the first plunger tip due to the movement. The first plunger tip may have a relatively hard end for engaging an intraocular lens.

Process 800 also calls for engaging an intraocular lens with the first plunger tip (operation 808). The intraocular lens may, for example, be stored in a lens chamber. Process 800 additionally calls for moving the intraocular lens into a delivery cartridge to fold the intraocular lens (operation 812). In some instances, portions of the intraocular lens (e.g., haptics) may have already been folded upon insertion in the lens chamber.

Process 800 calls for stopping the first plunger tip after it has traveled a predetermined distance (operation 816). The stoppage may, for example, be accomplished by an interface between the delivery cartridge and the first plunger tip. The stoppage may occur when the lens has been substantially folded.

Process 800 also calls for moving in a second direction along the longitudinal axis in response to the applied force being reduced (operation 820). In some implementations, the applied force may be reduced to zero. The movement in the second direction may, for example, be caused by a resilient member (e.g., a spring) that has been compressed during the movement in the first direction. Moving in a second direction along the longitudinal axis in response to the applied force being reduced may include returning the first plunger tip to its original position (e.g., in a plunger tip chamber).

Process 800 additionally calls for disengaging from the first plunger tip (operation 824). The disengagement may, for example, be accomplished by moving the first plunger tip in a lateral direction relative to the longitudinal axis. Thus, the first plunger tip may no longer be aligned with the longitudinal axis. A cassette in a plunger chamber may, for example, hold the first plunger tip, and movement of the cassette may cause the first plunger tip to move laterally.

Process 800 also calls for aligning a second plunger tip with the longitudinal axis (operation 828). Aligning the second plunger tip may, for example, be accomplished by laterally moving a cassette holding the second plunger tip so that it is aligned with the longitudinal axis.

Process 800 also calls for engaging the second plunger tip (operation 832). Engaging the second plunger tip may, for example, be accomplished by mating with the second plunger tip. Process 800 additionally calls for engaging the intraocular lens with the second plunger tip (operation 836). The second plunger tip may have a relatively soft end for engaging the intraocular lens. The intraocular lens may, for example, have been resting in a folded state in the delivery cartridge. Process 800 also calls for moving the intraocular lens further into the delivery cartridge to compress the intraocular lens (operation 840).

Although FIG. 8 illustrates one implementation of a process for compacting an intraocular lens, other processes for compacting an intraocular lens may include fewer, additional, and/or a different arrangement of operations. For example, a process may additionally call for moving, in response to a force being applied in the first direction along the longitudinal axis, a plunger into position along the longitudinal axis in anticipation of contact with the second plunger tip. Additionally, a process for compacting an intraocular lens may also include, for example, locking a cassette holding the plunger tips in a position in which the first plunger tip and/or the second plunger tip is aligned with the longitudinal axis. As another example, a process for compacting an intraocular lens may include placing the lens in a lens chamber. As a further example, a process may not include stopping the first plunger tip after it has traveled a predetermined distance. The advancement of the first plunger tip may, for example, be stopped by a user ceasing to activate a plunger (e.g., in response to resistance generated by the intraocular lens). As a further example, a process may include moving the folded, compressed intraocular lens through an insertion tip to inject the intraocular lens into an eye. This movement may, for example, be in response to a longitudinal force being applied to the plunger or a rotational force being applied to the plunger.

The various implementations discussed and mentioned herein have been used for illustrative purposes only. The implementations were chosen and described in order to explain the principles of the disclosure and the practical application and to allow those of ordinary skill in the art to understand the disclosure for various implementations with various modifications as are suited to the particular use contemplated. Thus, the actual physical configuration of components may vary. For example, the mentioned size(s) of components and their illustrated sizing relative to each other may vary based on application. Moreover, the shapes of one or more components may vary depending on application. Thus, the illustrative implementations should not be construed as defining the only physical size, shape, and relationship of components.

Various systems and processes for inserting an intraocular lens have been discussed, and several others have been mentioned or suggested. However, those skilled in the art will readily recognize that a variety of additions, deletions, substitutions, and modifications may be made to these systems and processes while still achieving insertion of an intraocular lens. Thus, the scope of protection should be judged based on the following claims, which may capture one or more aspects of one or more implementations.

The invention claimed is:

1. An intraocular lens insertion system, the system comprising:
   a lens chamber adapted to receive an intraocular lens;
   a delivery cartridge coupled to the lens chamber and adapted to fold and compress an intraocular lens as the intraocular lens is moved therethrough;
   a plunger adapted to be manipulated by a user;
   a plunger chamber adapted to allow the plunger to be moved therein along a longitudinal axis and move a plunger tip along the longitudinal axis; and
   a plunger tip chamber, the plunger tip chamber adapted to house a first plunger tip and a second plunger tip and to alternately switch between alignment of the first plunger tip and the plunger and alignment of the second plunger tip with the plunger,
   wherein the plunger tip chamber is laterally moveable so as to alternatingly align the first plunger tip and the second plunger tip with the plunger.

2. The system of claim 1, wherein the plunger tip chamber is adapted to switch between the plunger tips by altering which plunger tip is aligned with the longitudinal axis.

3. The system of claim 1, wherein the plunger tip chamber comprises a cassette adapted to hold the first plunger tip and the second plunger tip and to move laterally within the plunger tip chamber to align alternatingly the first plunger tip and the second plunger tip with the plunger.

4. The system of claim 3, wherein the cassette is adapted to lock into a first position in which the first plunger tip is aligned with the plunger and to lock into a second position in which the second plunger tip is aligned with the plunger.

5. The system of claim 1, wherein the plunger tip chamber comprises a spring adapted to compress when the first plunger tip is moved by the plunger and adapted to retract the first plunger tip and the plunger when the plunger is released.

6. The system of claim 1, wherein the plunger is adapted to engage the first plunger tip via abutting contact and wherein the plunger is adapted to engage the second plunger tip via an interlocking relationship.

7. The system of claim 1, wherein the lens chamber is adapted to prevent advancement of the first plunger tip beyond a predetermined distance.

8. The system of claim 7, wherein the predetermined distance corresponds to a distance associated with substantially folding an intraocular lens.

9. The system of claim 1, further comprising an insertion tip coupled to the delivery cartridge and adapted to be inserted in an eye for injection of a folded, compressed intraocular lens.

10. The system of claim 1, wherein the first plunger tip comprises a material having a first hardness and the second plunger tip comprises a material having a second hardness, and wherein the first hardness is substantially greater than the second hardness.

11. An intraocular lens insertion system, the system comprising:
    a lens chamber adapted to receive an intraocular lens;
    a delivery cartridge coupled to the lens chamber and adapted to fold and compress an intraocular lens as the intraocular lens is moved therethrough;
    a plunger adapted to be manipulated by a user;
    a plunger chamber adapted to allow the plunger to be moved therein along a longitudinal axis and move a plunger tip along the longitudinal axis; and
    a plunger tip chamber, the plunger tip chamber adapted to house a first plunger tip and a second plunger tip and to alternately switch between alignment of the first plunger tip and the plunger and alignment of the second plunger tip with the plunger,
    wherein the plunger tip chamber comprises a cassette adapted to hold the first plunger tip and the second plunger tip and to move laterally within the plunger tip chamber to align alternatingly the first plunger tip and the second plunger tip with the plunger.

12. The system of claim 11, wherein the cassette is adapted to lock into a first position in which the first plunger tip is aligned with the plunger and to lock into a second position in which the second plunger tip is aligned with the plunger.

13. An intraocular lens insertion system, the system comprising:
    a lens chamber adapted to receive an intraocular lens;
    a delivery cartridge coupled to the lens chamber and adapted to fold and compress an intraocular lens as the intraocular lens is moved therethrough;
    a plunger adapted to be manipulated by a user;
    a plunger chamber adapted to allow the plunger to be moved therein along a longitudinal axis and move a first intraocular lens-engaging plunger tip and a second intraocular lens-engaging tip along the longitudinal axis; and
    a plunger tip chamber, the plunger tip chamber adapted to house the first intraocular lens-engaging plunger tip and the second intraocular lens-engaging plunger tip and to alternately switch between alignment of the first intraocular lens-engaging plunger tip and the plunger and alignment of the second intraocular lens-engaging plunger tip with the plunger.

14. The system of claim 13, wherein the plunger tip chamber is adapted to switch between the first intraocular lens-engaging plunger tip and the second intraocular lens-engaging plunger tip by altering which of the first intraocular lens-engaging plunger tip and the second intraocular lens-engaging tip is aligned with the longitudinal axis.

15. The system of claim 13, wherein the plunger tip chamber is laterally moveable so as to alternatingly align the first intraocular lens-engaging plunger tip and the second intraocular lens-engaging plunger tip with the plunger.

16. The system of claim 13, wherein the plunger tip chamber comprises a cassette adapted to hold the first intraocular lens-engaging plunger tip and the second intraocular lens-engaging plunger tip and to move laterally within the plunger tip chamber to align alternatingly the first intraocular lens-engaging plunger tip and the second intraocular lens-engaging plunger tip with the plunger.

17. The system of claim 16, wherein the cassette is adapted to lock into a first position in which the first intraocular lens-engaging plunger tip is aligned with the plunger and to lock into a second position in which the second intraocular lens-engaging plunger tip is aligned with the plunger.

18. The system of claim 13, wherein the plunger tip chamber comprises a spring adapted to compress when the first intraocular lens-engaging plunger tip is moved by the plunger and adapted to retract the first intraocular lens-engaging plunger tip and the plunger when the plunger is released.

19. The system of claim 13, wherein the plunger is adapted to engage the first intraocular lens-engaging plunger tip via abutting contact and wherein the plunger is adapted to engage the second intraocular lens-engaging plunger tip via an interlocking relationship.

20. The system of claim 13, wherein the lens chamber is adapted to prevent advancement of the first intraocular lens-engaging plunger tip beyond a predetermined distance.

21. The system of claim 20, wherein the predetermined distance corresponds to a distance associated with substantially folding an intraocular lens.

22. The system of claim 13, further comprising an insertion tip coupled to the delivery cartridge and adapted to be inserted in an eye for injection of a folded, compressed intraocular lens.

23. The system of claim 13, wherein the first intraocular lens-engaging plunger tip comprises a material having a first hardness and the second intraocular lens-engaging plunger tip comprises a material having a second hardness, and wherein the first hardness is substantially greater than the second hardness.

* * * * *